(12) United States Patent
Blondel et al.

(10) Patent No.: US 11,903,659 B2
(45) Date of Patent: Feb. 20, 2024

(54) ROBOTIC DEVICE FOR A MINIMALLY INVASIVE MEDICAL INTERVENTION ON SOFT TISSUES

(71) Applicant: QUANTUM SURGICAL, Montpellier (FR)

(72) Inventors: Lucien Blondel, Montpellier (FR); Fernand Badano, Lyons (FR); Bertin Nahum, Castelnau-le-Lez (FR)

(73) Assignee: QUANTUM SURGICAL, Montpellier (FR)

( * ) Notice: Subject to any disclaimer, the term of this patent is extended or adjusted under 35 U.S.C. 154(b) by 107 days.

(21) Appl. No.: 16/762,876

(22) PCT Filed: Nov. 8, 2018

(86) PCT No.: PCT/FR2018/052769
§ 371 (c)(1),
(2) Date: May 8, 2020

(87) PCT Pub. No.: WO2019/092372
PCT Pub. Date: May 16, 2019

(65) Prior Publication Data
US 2020/0281667 A1    Sep. 10, 2020

(30) Foreign Application Priority Data

Nov. 9, 2017    (FR) ...................................... 1760553

(51) Int. Cl.
*A61B 34/30*    (2016.01)
*A61B 34/20*    (2016.01)
(Continued)

(52) U.S. Cl.
CPC .......... *A61B 34/30* (2016.02); *A61B 1/00149* (2013.01); *A61B 8/4218* (2013.01);
(Continued)

(58) Field of Classification Search
CPC ... A61B 34/30; A61B 1/00149; A61B 8/4218; A61B 10/0233; A61B 18/02;
(Continued)

(56) References Cited

U.S. PATENT DOCUMENTS

2006/0274071 A1* 12/2006 Bazin ...................... G06T 11/00
345/475
2008/0186378 A1    8/2008 Shen et al.
(Continued)

FOREIGN PATENT DOCUMENTS

| EP | 2468207 A1 | 6/2012 |
|---|---|---|
| WO | 9611624 A2 | 4/1996 |
| WO | 2017116512 A1 | 7/2017 |

OTHER PUBLICATIONS

International Search Report in PCT/FR2018/052769 dated Jan. 25, 2019.

*Primary Examiner* — Hien N Nguyen
(74) *Attorney, Agent, or Firm* — ARENTFOX SCHIFF LLP

(57) ABSTRACT

A robotic device for a minimally invasive medical intervention on soft tissues is provided. The robotic device uses a medical instrument having a robot arm having several degrees of freedom and having an end suitable for receiving the medical instrument, an image capture system suitable for capturing position information concerning the anatomy of the patient, a storage medium having a biomechanical model of the human body, a processing circuit configured to determine a position setpoint and an orientation setpoint for said medical instrument on the basis of the biomechanical model, on the basis of the position information and on the basis of a trajectory to be followed by the medical instrument in order to perform the medical intervention, and a (Continued)

control circuit configured to control the robot arm in order to place the medical instrument in the position setpoint and the orientation setpoint.

17 Claims, 1 Drawing Sheet

(51) Int. Cl.
| | |
|---|---|
| A61B 34/00 | (2016.01) |
| A61B 90/13 | (2016.01) |
| A61B 1/00 | (2006.01) |
| A61B 8/00 | (2006.01) |
| A61B 10/02 | (2006.01) |
| A61B 18/02 | (2006.01) |
| A61B 18/12 | (2006.01) |
| A61N 5/10 | (2006.01) |
| A61N 7/00 | (2006.01) |
| A61B 34/10 | (2016.01) |
| A61B 90/50 | (2016.01) |
| A61B 17/34 | (2006.01) |
| A61B 17/00 | (2006.01) |
| A61B 18/00 | (2006.01) |

(52) U.S. Cl.
CPC .......... *A61B 10/0233* (2013.01); *A61B 18/02* (2013.01); *A61B 18/12* (2013.01); *A61B 34/20* (2016.02); *A61B 34/25* (2016.02); *A61B 90/13* (2016.02); *A61N 5/10* (2013.01); *A61N 7/00* (2013.01); *A61B 17/3494* (2013.01); *A61B 2017/00199* (2013.01); *A61B 2017/00203* (2013.01); *A61B 2018/00613* (2013.01); *A61B 2034/105* (2016.02); *A61B 2034/107* (2016.02); *A61B 2034/2051* (2016.02); *A61B 2034/2055* (2016.02); *A61B 2034/742* (2016.02); *A61B 2034/743* (2016.02); *A61B 2090/502* (2016.02)

(58) Field of Classification Search
CPC ......... A61B 18/12; A61B 34/20; A61B 34/25; A61B 90/13; A61B 17/3494; A61B 2017/00199; A61B 2017/00203; A61B 2018/00613; A61B 2034/105; A61B 2034/107; A61B 2034/2051; A61B 2034/2055; A61B 2034/742; A61B 2034/743; A61B 2090/502; A61B 34/10; A61B 90/361; A61B 90/37; A61B 2034/2057; A61B 2034/2065; A61N 5/10; A61N 7/00

See application file for complete search history.

(56) References Cited

U.S. PATENT DOCUMENTS

| | | | |
|---|---|---|---|
| 2010/0063514 A1 | 3/2010 | Maschke | |
| 2011/0257514 A1 | 10/2011 | Bucki et al. | |
| 2015/0065793 A1* | 3/2015 | Diolaiti | A61B 5/065 |
| | | | 600/102 |
| 2015/0366546 A1 | 12/2015 | Kamen et al. | |
| 2016/0184032 A1* | 6/2016 | Romo | A61B 10/04 |
| | | | 901/46 |
| 2016/0206381 A1* | 7/2016 | Grass | A61B 5/066 |
| 2016/0236009 A1* | 8/2016 | Sabczynski | A61N 5/1037 |
| 2017/0265947 A1 | 9/2017 | Dyer et al. | |

* cited by examiner

ROBOTIC DEVICE FOR A MINIMALLY INVASIVE MEDICAL INTERVENTION ON SOFT TISSUES

CROSS-REFERENCE TO RELATED APPLICATIONS

This application is a National Stage Entry of PCT/FR2018/052769, filed Nov. 8, 2018, which claims foreign priority to FR Patent Application No. 1760553 filed on Nov. 9, 2017, the disclosure of which is hereby incorporated by reference in its entirety.

TECHNICAL FIELD

The present invention belongs to the field of medical interventions and relates more particularly to a robotic device for minimally invasive medical interventions performed on the deformable tissues of a patient, for example for performing treatment or diagnosis on deformable organs or anatomical structures.

BACKGROUND

Medical interventions (for diagnosis, therapy and/or surgery) by a minimally invasive or percutaneous route are becoming increasingly important, especially in oncology for the local treatments of cancer, acting directly on the cells of the affected organ, such as the liver, the kidneys, the lungs, the pancreas, the breasts, the prostate, etc.

Outside the field of oncology, there are many medical procedures and applications using a minimally invasive or percutaneous access route, for example by insertion of a needle: biopsies (collecting tissues for pathological analysis), placement of drains (aspiration of fluids), injection of therapeutic products (treatment of pain), etc.

In contrast to open or conventional surgery, which may require an incision measuring several tens of centimeters, minimally invasive medical interventions at most use small incisions or openings through which are introduced an endoscope, a probe, a needle or other medical instruments, in order to reach, view and/or treat the targeted anatomical zone.

Minimally invasive medical interventions can afford many benefits such as limiting pain and surgical trauma, reducing bleeding during a surgical intervention, and reducing the length of hospitalization. They allow the medical intervention to be performed in outpatient surgery, which permits faster recovery of the patient, less scarring, a reduced risk of infection, etc.

In addition to the conventional technique of surgical resection using forceps, scissors and other medical instruments, several technologies for destroying tissues by a minimally invasive or percutaneous route have been validated or are in the course of evaluation. Mention may be made, for example, of laser surgery, cryotherapy, treatment by radiofrequency, microwaves, electroporation, or even focused ultrasound and curie therapy. A common feature of most of these techniques is that a very small incision is made and one or more needles, probes or electrodes for delivering precise and localized treatment (thermal, non-thermal or radioactive treatment) are inserted as far as the targeted anatomical zone.

The medical interventions performed by a minimally invasive route in most cases require the operator to insert a medical instrument inside the body of the patient as far as a certain depth in order to reach the targeted anatomical zone. These procedures are sometimes lengthy and difficult since, in contrast to open surgery, the operator does not always have a direct view of the anatomy of the patient and of the organ that is to be treated. This complicates the identification of the anatomical structures, the precise placement of the medical instrument and avoidance of sensitive anatomical structures (nerves, vessels, healthy organs, etc.).

The surgeons can use pre-operative medical images (computed tomography (CT), magnetic resonance imaging (MRI), radiography, etc.), which have been taken for diagnostic purposes, in order to make it easier to register the anatomy and to plan the medical intervention in advance. The pre-operative images provide a representation of the anatomy that is valid at a given moment: not the moment when the medical intervention is performed, but a moment previous to this.

In order to introduce the medical instrument correctly inside the body of the patient as far as the desired position and depth, without damaging the sensitive anatomical structures during the operation, the operator has to know where the instrument is situated inside the body of the patient. Several systems and methods are nowadays available for determining the position and the orientation of the medical instrument during a minimally invasive intervention when the direct view of the anatomy is not available through a microscope or an endoscope.

Navigation systems (or computer-assisted surgery) guided by the image allow the position and the orientation of a medical instrument to be tracked in real time, by displaying a virtual medical instrument superposed on images of the body of the patient. They use 3D locating technologies to register both the patient and the medical instrument, the most widespread being of the optical or electromagnetic type.

The use of an image capture system is necessary before, at the start of and/or during the medical intervention in order to capture one or more images of the patient (by scans, MRI, X-rays, ultrasound, etc.). Before commencing the medical intervention, these images are coordinated with the real position of the anatomy of the patient placed on the operating table, by various known methods of registration, such as rigid or deformable registration of noteworthy points and/or surfaces, or referencing of the position of the image capture system itself.

Optical navigation systems register the position of the medical instrument by means of infrared cameras and emitters or reflectors placed according to a known geometry on the medical instrument and on the patient, in order to serve as a reference and in order to track its movements.

Electromagnetic navigation systems register the position of the medical instrument by means of a low-intensity magnetic field generator placed near the body of the patient, sensors which can be incorporated in the medical instrument, and reference sensors placed on the patient. These electromagnetic navigation systems are compact and do not suffer from the problem of obstruction of the field of view in optical navigation systems. However, they require a specific and restricting environment linked to the presence of a magnetic field formed by the magnetic field generator.

Although all of these known navigation systems are able to improve the precision of the medical procedure compared to the conventional manual method, by supplying in real time the position and the orientation of the medical instrument in images, they have important limitations in respect of minimally invasive medical interventions on deformable tissues.

A first limitation is that the final procedure of introducing the medical instrument as far as the targeted anatomical zone is performed manually by the operator, which means that the result depends on the skill of the operator and is unable to attain a high degree of precision.

A second limitation is that the functioning of these navigation systems assumes that the targeted organs or anatomical structures do not move and do not deform between the moment when the reference examination is carried out and the moment when the operator introduces the medical instrument. In the case where the examination has been carried out several days before the medical intervention, and with the patient in a different position on the operating table compared to his position on the examination table, the targeted organs or anatomical structures may have moved or been deformed, and the offset between the displayed position and the real position of the targeted organ or anatomical structure may introduce a high degree of imprecision. In addition, the targeted organs or anatomical structures may deform simply on account of the respiration of the patient, and the known navigation systems are based on controlling the respiration by the patient, which greatly limits the precision attainable by these navigation systems.

There are also robotic devices for assisting in the medical procedure for minimally invasive surgery.

In particular, the patent U.S. Pat. No. 8,795,188 discloses a system for a medical intervention on a patient, which system comprises a robot, a device for recording the movements of the patient, and a method for automatically taking account of the periodic movements of the patient, typically the movements of the thoracic cage due to respiration.

However, the variants describing the use of navigation technology or of a continuous laser scanner require a capture of images prior to the operation and assume that the targeted organ or anatomical structure does not move and does not deform with respect to the outer envelope of the patient (skin). The variant describing the use of images of the X-ray type during the intervention requires the complex and irradiating placement of a continuous image capture system.

In addition, the above-described limitations in the case of a medical intervention requiring the insertion of a medical instrument inside the body of the patient can be generalized to cover medical interventions that do not require introduction of a medical instrument into the body of the patient. For example, in the case of an instrument providing treatment by focused ultrasound, it must also be possible to control the path of the ultrasound waves inside the body of the patient as far as the targeted anatomical zone inside the body of said patient, to which zone said ultrasound waves have to be focused.

SUMMARY

The object of the present invention is to overcome all or some of the limitations of the solutions from the prior art, especially those set out above, by making available a solution that helps the operator to position a medical instrument with respect to an organ or an anatomical structure in the body of a patient, with the aim of performing a diagnosis or a localized therapeutic treatment, taking into account the fact that the organ or the anatomical structure may move or deform inside the body of the patient.

To this end, and according to a first aspect, the invention relates to a robotic device for performing a medical intervention on a patient using a medical instrument, comprising:
  a robot arm having several degrees of freedom and having an end suitable for receiving the medical instrument,
  an image capture system suitable for capturing position information concerning the anatomy of the patient,
  a storage medium having a biomechanical model of the anatomical structures of the human body,
  a processing circuit configured to determine a position setpoint and an orientation setpoint for said medical instrument on the basis of the biomechanical model, on the basis of the position information and on the basis of a trajectory to be followed by the medical instrument in order to perform the medical intervention,
  a control circuit configured to control the robot arm in order to place, or help to place, the medical instrument in the position setpoint and the orientation setpoint.

By virtue of the robotic arm, the precision and reproducibility of the positioning of the medical instrument are much better than that of an operator. This gain in precision means that the treatment chosen by the operator can be performed very close to the target organ or the target anatomical structure, and the clinical efficacy of the treatment can thus be improved. It is possible to envision the treatment of lesions that are inoperable because they are too small or are situated close to or inside critical zones. The precision and reproducibility also make it possible to reduce the risks of complications such as hemorrhages, pain and loss of function resulting from damage caused to sensitive anatomical structures present on the trajectory, following manual errors in the positioning of the medical instrument.

The robotic device also uses the a priori knowledge of a biomechanical model of the human body.

A "biomechanical model" of the human body is understood as a mathematical model of the various anatomical structures (muscles, tendons, bone structures, organs, vascular network, etc.) of the human body, and therefore of the patient, in the anatomical zone in question, which permits modeling of the deformations of said anatomical structures and also of the mechanical interactions between said anatomical structures. Such a biomechanical model thus makes it possible in particular to determine the deformations and mechanical interactions (hence movements) of the internal anatomical structures of the patient that are induced, for example, by a modification of the outer envelope of said patient, a modification of the positions of the vessels of an organ, a modification of the outer envelope of an organ, etc. Such modifications may be induced, for example, by the respiration of the patient (movement of the organs induced by the movement of the thoracic cage and diaphragm), by a change of position of said patient (movement of the organs induced by gravity), by contact with a medical instrument (local deformation), etc. The anatomical zone in question corresponds, for example, to the thoracic zone and/or the abdominal zone and/or the pelvic zone of the patient.

Thus, the robotic device uses the trajectory, the biomechanical model and the position information acquired during the medical intervention to determine the real position of a movable and deformable anatomical structure in the body of the patient, irrespective of the position of the patient on the operating table and of the level of his/her respiration. This functionality greatly enhances the performance of the medical intervention by avoiding the errors due to the operator compensating for the movements associated with respiration and with the internal deformations of the organs, which are not taken into account by the navigation systems and robotic systems known from the prior art.

For all of these reasons, the robotic device is particularly suitable for minimally invasive medical interventions on deformable tissues of a patient.

In particular embodiments, the robotic device can additionally have one or more of the following features, either individually or in all technically possible combinations.

In particular embodiments, the biomechanical model models the anatomical structures of the human body in the thoracic zone and/or the abdominal zone and/or the pelvic zone.

In particular embodiments, the image capture system is of a non-irradiating type.

In fact, by virtue of taking into account the biomechanical model, the image capture system used during the intervention can be non-irradiating. "Non-irradiating" is understood to mean that no ionizing radiation (in particular X-rays) is generated in the direction of the patient in order to capture the images during the medical intervention. The irradiation dose is therefore greatly reduced, both for the patient and for the medical team located near the image capture system. In addition, the image capture system may be much less expensive and less cumbersome than a CT scanner, for example, such that the robotic device can be used even in small operating theaters without a CT scanner, which makes its use much less restricted.

In particular embodiments, the image capture system has at least one so-called non-contact device suitable for capturing position information without contact with the patient.

In particular embodiments, the image capture system has at least one of the following non-contact devices: a stereoscopic camera, a structured-light camera, a time-of-flight camera, a depth measurement camera, etc.

In particular embodiments, the image capture system is suitable for supplying position information corresponding to the position of an outer surface of the body of the patient.

In particular embodiments, the image capture system has at least one so-called contact device suitable for capturing position information by contact with the patient.

In particular embodiments, the image capture system has at least one of the following contact devices: an ultrasound probe, an endoscope, etc.

In particular embodiments, the image capture system is composed of one or more non-contact devices, that is to say the image capture system, more generally the robotic device, has exclusively one or more non-contact devices and is without any contact device for capture of images.

In particular embodiments, the control circuit is configured to control the robot arm according to at least one of the following modes: an automatic mode, a collaborative mode, an automatic tracking mode, a collaborative tracking mode, etc.

In particular embodiments, the processing circuit is configured to determine or assist in determining the trajectory of the medical instrument on the basis of images of the patient.

In particular embodiments, the processing circuit is configured to regulate or assist in regulating parameters of a treatment that is to be carried out during the medical intervention, by simulation of the effects of said parameters on the basis of images of the patient.

In particular embodiments, the robotic device has a guide tool suitable for guiding the medical instrument, fixed or intended to be fixed to an end of the robot arm.

In particular embodiments, the robotic device has at least one man-machine interface device from among the following devices: a display screen, a touch sensitive display screen, a keyboard, 2D and/or 3D goggles, a joystick, a movement detection module, a voice-activated control module, etc.

In particular embodiments, the robotic device has at least one device for registering a point of entry from among the following devices: a medical instrument with an atraumatic tip, a laser targeting module, etc.

In particular embodiments, the medical instrument is one of the following medical instruments: a biopsy needle, a catheter, an endoscope, or even a treatment instrument using focused ultrasound, a laser treatment instrument, an instrument for treatment by cryotherapy, an instrument for treatment by radiofrequency, an instrument for treatment by electroporation, an instrument for treatment by curie therapy, etc.

In particular embodiments, the robotic device has a mobile carriage carrying the robot arm, said mobile carriage having immobilizing means.

BRIEF DESCRIPTION OF DRAWINGS

The invention will be better understood on reading the following description given as a non-limiting example, with reference being made to the figures, in which.

In these figures, references that are identical from one figure to another designate identical or similar elements. For reasons of clarity, the elements shown are not to scale, unless stated otherwise.

DETAILED DESCRIPTION OF EMBODIMENTS

Figure 1:
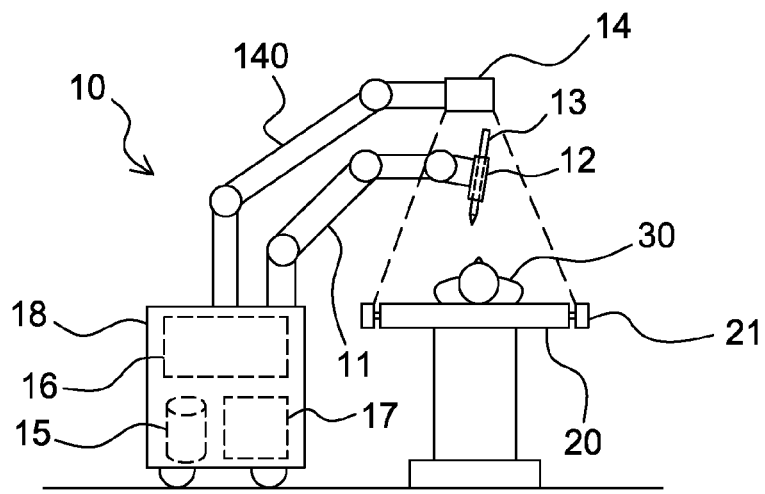
FIG. 1 shows a schematic view of an embodiment of a robotic device for minimally invasive medical interventions on soft tissues.

FIG. 1 shows schematically an embodiment of a robotic device 10 for assisting an operator in a medical intervention, for example a minimally invasive intervention on soft tissues.

As is illustrated in FIG. 1, the robotic device 10 has a robot arm 11 with several degrees of freedom. The robot arm 11 has an end suitable for receiving a medical instrument 13. In the example shown in FIG. 1, the medical instrument 13 is mounted on the end of the robot arm 11 by way of a guide tool 12 suitable for guiding said medical instrument 13. For this purpose, the robot arm 11 has, at said end, an interface suitable for receiving said guide tool 12.

The robot arm 11 preferably has at least 6 degrees of freedom in order to permit wide ranges for spatially monitoring the position and orientation of the guide tool 12 with respect to a patient 30, who is lying on an operating table 20 for example.

The guide tool 12 is suitable for guiding the medical instrument 13, that is to for constraining the displacement of said medical instrument 13 with respect to said guide tool 12. For example, the guide tool 12 is a slide suitable for guiding the medical instrument 13 in translation, so as to constrain the displacement of said medical instrument 13, for example during its insertion into the body of the patient 30.

The guide tool 12 is, for example, fixed removably to the robot arm 11, which is preferably suitable for receiving different types of guide tools 12, for example associated with different medical instruments 13 and/or different medical procedures.

The interface of the robot arm 11 can have, for example, an error prevention mechanism for ensuring a correct mounting of the guide tools 12 on the robot arm 11. In preferred embodiments, the interface can additionally have an electronic system for automatically identifying the guide tool 12 mounted by the operator, in order thereafter to use the characteristics of the guide tool 12 in the calculations, for example its reference, its dimensions, its weight, its center of gravity, and any other data useful for its function or its performance.

The robotic device 10 is preferably suitable for receiving, on a guide tool 12 carried by the robot arm 11, any type of medical instrument 13, in particular any type of medical instrument used for minimally invasive interventions on soft tissues. For example, the robotic device 10 is preferably suitable for receiving and moving at least one of the following surgical medical instruments:
- a biopsy needle,
- a catheter,
- an endoscope,
- a treatment instrument using focused ultrasound,
- a laser treatment instrument,
- an instrument for treatment by cryotherapy,
- an instrument for treatment by radiofrequency,
- an instrument for treatment by electroporation,
- an instrument for treatment by curie therapy, etc.

The robotic device 10 also has a control circuit 16 suitable for controlling the robot arm 11 in order to modify the position and orientation of the guide tool 12 in a reference frame associated with the robotic device 10. The control circuit 16 has, for example, one or more processors and storage means (magnetic hard disk, electronic memory, optical disk, etc.) in which a computer program product is stored in the form of a set of program code instructions to be executed in order to control the robot arm 11. Alternatively or in addition, the control circuit 16 has one or more programmable logic circuits (FPGA, PLD, etc.) and/or one or more specialized integrated circuits (ASIC, etc.), and/or a set of discrete electronic components, etc., suitable for controlling said robot arm 11.

By virtue of the control circuit 16, the robot arm 11 and the guide tool 12 carried by the robot arm 11, it is possible for the medical instrument 13 to be positioned, oriented and guided with much greater precision than in the case of a medical instrument 13 manipulated directly by an operator.

In the example illustrated in FIG. 1, the robotic device 10 has a mobile carriage 18, for example mounted on wheels, on which the robot arm 11 is mounted. Such arrangements are particularly advantageous in the sense that it is then particularly easy to move the robot arm 11 from one side of the operating table to another, from one side of an operating theater to another, etc. The carriage 18 has immobilizing means (not shown in the figures) by which the carriage 18 can be immobilized with respect to the operating table 20. The immobilizing means can be of any suitable type and can have, in particular, brakes on the wheels, retractable pads or feet, systems for mechanical attachment to the operating table 20, systems for mechanical attachment to the ground, etc.

Figure 2:
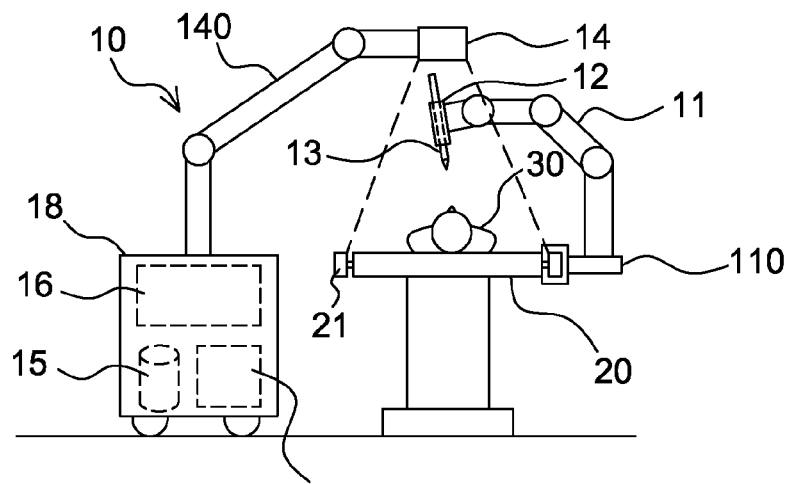
FIG. 2 shows a schematic view of an alternative embodiment of the robotic device from FIG. 1.

However, according to other examples, there is nothing to exclude the robot arm 11 being mounted directly on the operating table, either removably or permanently (in which case the operating table is an integral part of the robotic device 10). FIG. 2 shows schematically an alternative embodiment of the robotic device 10 in which the robot arm 11 is mounted removably on the operating table 20. In the example illustrated in FIG. 2, the robot arm 11 is mounted on a support 110 forming a rigid mechanical link to rails 21 of the operating table 20.

As is illustrated in FIGS. 1 and 2, the robotic device 10 also has an image capture system 14 suitable for capturing position information concerning the anatomy of the patient 30 in the reference frame associated with the robotic device 10, or in a frame different from said reference frame for which the matrix of passage to said reference frame is known a priori or can be determined. In preferred embodiments, the image capture system 14 is of a non-irradiating type, so as to limit the irradiation dose to which the patient 30 and the medical team are exposed.

The image capture system 14 makes it possible to capture position information concerning the anatomy of the patient 30. The position information concerning the anatomy of the patient 30 corresponds, for example, to the position of the outer surface of the body of the patient 30 in the reference frame, the position of the bone structure of said body of the patient 30 in the reference frame, the position of an organ or vessels inside said body of the patient 30 in the reference frame, etc.

Generally, any type of image capture system 14 suitable for supplying position information concerning the anatomy of the patient 30 can be used in the robotic device 10. For example, the image capture system 14 can have one or more so-called non-contact devices suitable for capturing position information without contact with the patient 30 and/or one or more so-called contact devices suitable for capturing position information by contact with the patient 30. The image capture system of the robotic device preferably has exclusively one or more non-contact devices and is without any contact device.

In particular embodiments, the image capture system 14 has at least one of the following non-contact devices:
- a stereoscopic camera,
- a structured-light camera,
- a time-of-flight camera (ToF camera),
- a depth measurement camera (for example an RGB-D camera), etc.

Such non-contact devices make it possible, for example, to capture position information representative of the position of the outer surface of the body of the patient 30 with respect to the non-contact device.

In particular embodiments, the image capture system 14 has at least one of the following contact devices:
- an ultrasound probe (capture by non-intrusive contact),
- an endoscope (capture by intrusive contact), etc.

Such contact devices make it possible, for example, to capture position information representative of the position of an organ or of vessels inside the body of the patient 30.

The image capture system 14 is, for example, integrated in the robot arm 11 or mounted at the end of said robot arm 11.

In the examples illustrated in FIGS. 1 and 2, the image capture system 14 is mounted on a support distinct from the robot arm 11. The support is, for example, an articulated arm 140, optionally motorized, in which case it forms a robot arm distinct from the robot arm 11 carrying the guide tool 12 of the medical instrument 13. In the example shown in FIG. 1, the articulated arm 140 is carried, like the robot arm 11, by the mobile carriage 18. In the example illustrated in FIG. 2, the articulated arm 140 carrying the image capture system 14 is carried by a mobile carriage 18.

Moreover, according to other examples, there is nothing to exclude having an image capture system 14 carried by the operator for obtaining position information concerning the anatomy of the patient 30.

The position and the spatial orientation of the image capture system 14 are, for example, known in the reference frame of the robotic device 10, either from knowledge of its geometry when it is carried by the robot arm 11, or through use of a 3D location system, such as an optical, electromagnetic or other kind of navigator.

As is illustrated in FIGS. 1 and 2, the robotic device 10 likewise has a storage medium 15 storing a biomechanical model of the anatomical structures of the human body. In the examples illustrated in FIGS. 1 and 2, the storage medium 15 is represented as being distinct from the control circuit 16. However, according to other embodiments, the storage medium 15 can also be one of the storage means of said control circuit 16.

It will be noted that the biomechanical model of the human body is not necessarily specific to the patient 30 under consideration and can be a biomechanical model of a generic patient, for example of the same sex, height, build, etc., as the patient 30 on whom the medical procedure is to be performed. The biomechanical model preferably includes the principal anatomical structures of the thoracic, abdominal and pelvic zone, such as the thoracic and abdominal walls, the muscles, tendons, bones and joints, organs, vascular system, etc., and also their models of deformation and their mechanical interactions. The biomechanical model also preferably takes account of the effects of gravity depending on the position of the patient 30.

Such biomechanical models are known in the scientific literature, see the following publications for example:
  "SOFA: A Multi-Model Framework for Interactive Physical Simulation", F. Faure et al., Soft Tissue Biomechanical Modeling for Computer Assisted Surgery—Studies in Mechanobiology, Tissue Engineering and Biomaterials, volume 11, Springer,
  "A Personalized Biomechanical Model for Respiratory Motion Prediction", B. Fuerst et al., International Conference on Medical Image Computing and Computer Assisted Intervention, 2012,
  "Patient-Specific Biomechanical Model as Whole-Body CT Image Registration Tool", Mao Li et al., Medical Image Analysis, 2015, May, pages 22-34.

The biomechanical model can be created, for example, by the transcription of a database of three-dimensional medical images (CT scans, MRI scans, etc.). The geometry of the structures of interest can be extracted from the medical images by algorithms of segmentation and reconstruction. The analysis of the image database makes it possible to calculate an average geometry of the components of the biomechanical model and also the main parameters of deformation representative of all the medical images of the database. It is possible to assign, to each of the structures, mechanical characteristics and different boundary conditions in order to create a biomechanical model thereof. The biomechanical model preferably includes modeling of the musculoskeletal system composed of the bones, muscles, tendons, ligaments and cartilage.

As is illustrated in FIGS. 1 and 2, the robotic device 10 also has a processing circuit 17. The processing circuit 17 is configured to determine a position setpoint and an orientation setpoint for the guide tool 12 on the basis of the biomechanical model of the anatomical structures of the human body, and on the basis of the position information captured by the image capture system 14.

The processing circuit 17 has, for example, one or more processors and storage means (magnetic hard disk, electronic memory, optical disk, etc.) in which a computer program product is stored in the form of a set of program code instructions to be executed in order to determine the position setpoint and the orientation setpoint. Alternatively or in addition, the processing circuit 17 has one or more programmable logic circuits (FPGA, PLD, etc.), and/or one or more specialized integrated circuits (ASIC, etc.), and/or a set of discrete electronic components, etc., suitable for determining the position setpoint and the orientation setpoint.

In the examples illustrated in FIGS. 1 and 2, the processing circuit 17 is shown as being distinct from the control circuit 16. However, according to other embodiments, the processing circuit 17 can be merged with, or use devices also used by, said control circuit 16. In addition, the storage medium 15 is shown as being distinct from the processing circuit 17. However, according to other embodiments, the storage medium 15 can also be one of the storage means of said processing circuit 17.

The position setpoint and the orientation setpoint for the guide tool 12 are additionally determined on the basis of a trajectory to be followed by the medical instrument 13 during the medical intervention.

In the case of a medical intervention that requires introducing the medical instrument 13 into the body of the patient 30, the trajectory corresponds to the trajectory which the medical instrument 13 has to travel inside the body of the patient 30 and along which said medical instrument must be guided during the medical intervention. For example, the trajectory corresponds to the position of a point of entry, for example on the outer surface of the anatomy of the patient 30, through which the medical instrument 13 has to penetrate into the body of the patient 30, and also the position of a target point inside the patient 30, at the area of the targeted anatomical structure to be reached by said medical instrument 13. The point of entry and the target point are, for example, stored in the form of coordinates in a frame associated with the anatomy of the patient 30.

In the case of a medical intervention that does not require introducing the medical instrument 13 into the body of the patient 30, for example in the case of an instrument for treatment by focused ultrasound, the trajectory corresponds to the trajectory on which the ultrasound waves have to travel inside the body of the patient 30. For example, the trajectory corresponds to the position of a point of entry, for example on the outer surface of the anatomy of the patient 30, through which the ultrasound waves have to penetrate into the body of the patient 30, and also the position of a target point inside the patient 30, on which point the ultrasound waves have to be focused. The point of entry and the target point are, for example, stored in the form of coordinates in a frame associated with the anatomy of the patient 30.

The trajectory can be predetermined by means other than the robotic device 10, in which case it is stored, for example, in the storage medium 15 prior to the medical intervention. Alternatively or in addition, the trajectory can also be determined by means of the robotic device 10, as is described in the description below.

For example, the processing circuit 17 incorporates algorithms for coordinating the biomechanical model with the position information concerning the anatomy of the patient 30, which information is supplied by the image capture system 14. Thus, the processing circuit 17 can determine the position and orientation of the patient 30 in the reference frame associated with the robotic device 10. The processing circuit 17 can also determine the position of the point of entry and the position of the target point of the trajectory in said reference frame, taking account of the deformations of the anatomical structures (caused by gravity, respiration, mechanical contact with a medical instrument, etc.) of the patient with respect to the anatomical structures of the patient 30 under consideration in order to determine said trajectory. For example, an algorithm makes it possible to propagate the movements of the surface of the skin to the internal volume and to calculate correctly the position of the internal anatomical structures. According to another example, it is possible to determine the position and the deformation of an organ from information concerning the position of the vessels of this organ (position information supplied, for example, by an ultrasound probe). According to another example, it is possible to determine the position and the deformation of an organ from information concerning the position of the outer surface of said organ (position information supplied, for example, by an endoscope). The capture of the information concerning the position of the anatomy of the patient 30 and the calculation for coordinating the biomechanical model with said information concerning the position of the anatomy of the patient 30 are preferably carried out in real time or almost in real time, such that the position of the point of entry and the position of the target point in the reference frame can be updated in real time or almost in real time in order to monitor the movements and deformations of the anatomical structures of the patient 30. This updating can also be carried out during the insertion of the medical instrument 13 into the body of the patient 30, in order to take account of the deformations induced by the movement of said medical instrument 13.

Having determined the parameters of the trajectory (positions of the point of entry and of the target point) in the reference framework associated with the robotic device 10, or simultaneously with this determination, the processing circuit 17 determines a position setpoint and an orientation setpoint of the guide tool 12 in order to comply with said trajectory.

The control circuit 16 can then control the robot arm 11 to place, or to help the operator place, the guide tool 12 in said position setpoint and said orientation setpoint that are determined by the processing circuit 17. In preferred embodiments, the control circuit 16 is suitable for controlling the robot arm 11 according to at least one of the following modes:
  an automatic mode,
  a collaborative mode,
  an automatic tracking mode,
  a collaborative tracking mode.

In the automatic mode, the control circuit 16 moves the robot arm 11 from its current position and orientation to the position setpoint and the orientation setpoint by automatically calculating the trajectory between the current position and the position setpoint.

Overview—Basics of Algorithm

Initial Computation

The following paragraphs describe one implementation to compute the positions of the entry and target points (trajectory) in the robot reference frame, in the case where the image capture system supplies position information corresponding to the position of the outer surface of the patient's body (skin).

For this computation, the following transformation matrix can be used:
$$_R M^C \times_C M^{PS} \times (_I M^{PS})^{-1} \times P\_I = P\_R$$
  M=matrix
  R=robot base
  C=camera
  PS=patient skin
  I=medical image
  T=trajectory defined in medical image
  P=entry point, target point P_I: The coordinates of either the entry or target point P on the planned trajectory with respect to the medical image reference frame (I) is known at the end of the intervention planning phase by having defined the entry point and the target point positions in the medical images (e.g. CT scan). During the scan acquisition, the patient is in a specific phase of the respiratory cycle, e.g. full expiration (FE) or full inspiration (FI).

$_I M^{PS}$: The pose of the patient skin (PS) can be calculated in the medical image reference frame (I) by means of manual, semi-automatic or automatic segmentation with state-of-the-art conventional algorithms.

$_C M^{PS}$: The pose of the patient skin (PS) with respect to the camera reference system (C) is provided by the image capture system, i.e. camera. The reference pose is captured when the patient is in the same specific phase of the respiratory cycle, e.g. full expiration (FE) or full inspiration (FI), as during the image acquisition.

$_R M^C$: The pose of the camera (C) with respect to the robot reference frame (R) can be provided by several ways. One simple solution is to have the camera in a fixed position relative to the robot cart baseplate, this position being calibrated during the manufacturing process of the device. Another solution is to have a camera mounted on an articulated arm fixed to a predefined or calibrated position on the robot cart baseplate. The articulated arm has joints with position sensors so that when the camera position is moved relative to the robot cart baseplate, the system can compute the pose of the camera in real-time with the forward kinematics model.

P_R: the coordinates of the point P of the planned trajectory is known is the robot reference frame.

Update of the Position with Movement of the Patient Skin (Translation, Rotation)

When the patient is translated by table motion or rotated, the pose of the patient skin is captured by the camera. This new pose can be fed into the equation $_R M^C \times_C M^{PS} \times (_I M^{PS})^{-1} \times P\_I = P\_R$ (outlined above) to compute up-to-date positions of entry and target point in the robot reference frame matching the new position and orientation of the patient.

Update of the Position with Deformation of the Patient Skin

When the patient breathes, the deformation of the patient skin is captured by the camera as the difference between the current pose and the reference pose of the patient skin. At this stage, the biomechanical model is used to compute the new positions of the entry and target points that were impacted by the breathing.

In a first preliminary phase, the biomechanical model is adjusted and registered to the patient anatomy during the intervention planning phase.

This consists in using the dimensional characteristics of the patient anatomy that are extracted from the medical images to serve as parameters that adjust the biomechanical model to the patient's size and shape. Such dimensions can be major organs and bones 2D dimensions in axial, coronal or sagittal planes, or specific distances between organs, bones or skin in axial, coronal or sagittal planes. Another way to adjust the biomechanical model is to use atlas-based deformation techniques to determine a deformation field to be applied to one or several bio-mechanical models (from an atlas). The deformation field and the final chosen biomechanical model is determined after optimization of a cost function (similarity measurements, deformation energy) to match the actual anatomy of the patient.

Once the biomechanical model has been properly adjusted and matches the patient anatomy, it can be registered to the medical images reference frame (I). This can be calculated using the position of the patient skin (PS) in both the medical images and the biomechanical model and state-of-the-art algorithms, for example, Iterative Closest Point, Rigid Registration, and Non-Rigid Registration among others known in the art, that matches point clouds or surface with conventional algorithms such as rigid or elastic registration.

Since the biomechanical model is now registered to the patient images (I), the positions of the entry point and target point inside the model are known, meaning each point is located within an anatomical structure with bio-mechanical parameters known from the model.

Based on known parameters, such as the needle or instrument used, the point of puncture (on the skin), the trajectory path inside the anatomy, and based on real time measurements (such as the force applied during insertion on the robot end effector, and the resulting response forces from the crossed anatomy, or the deformation of the patient skin surface), the bio-mechanical model can be used to update the positions of any point of the planned trajectory, such as the target point.

In this case, the following computation is used:
$$_R M^C \times_C M^{PS} \times (_I M^{PS})^{-1} \times (_I M^T, BM, p) =_R M^T$$
where $f(_I M^T, BM, p)$ is the time-varying function applying the registered biomechanical model BM to the planned trajectory $_I M^T$, knowing the set of parameters measured in real time (such as forces measured at and effector, or the deformation of the patient skin surface).

In the collaborative mode, the control circuit 16 moves the robot arm 11 in the direction of the forces exerted by the operator, it being possible for these forces to be exerted on the guide tool 12 or on one of the shafts of the robot arm 11. The forces are measured and calculated by virtue of one or more sensors (not shown in the figures) equipping the end of the robot arm 11 and/or each of its shafts. Geometric constraints can be integrated in the collaborative mode in order to restrict the movements of the robot arm 11 and thus facilitate the medical procedure. For example, the movements can be constrained in a zone, outside a zone, along an axis or a curve, about a point, etc. The constraint can be defined by any type of geometric shape and associated behavior (inclusion/exclusion). In the collaborative mode, the control circuit 16 helps the operator place the guide tool 12 in the position setpoint and the orientation setpoint.

In the tracking mode, the control circuit 16 moves the robot arm 11 in the direction of the movements of the patient 30 in order to place the guide tool 12 in the position setpoint and the orientation setpoint that are updated in real time or almost in real time by the processing circuit 17. In this case, the medical instrument 13 moves in the reference frame associated with the robotic device 10 but remains substantially immobile during the time in a frame associated with the target organ.

In the collaborative tracking mode, the control circuit 16 moves the robot arm 11 in the direction of the movements of the patient 30, with a flexibility about the controlled position. For example, the operator can exert forces on the guide tool 12 and is able to deviate the position of the guide tool 12, slightly and temporarily, from the position setpoint and the orientation setpoint. The robot arm 11 exerts forces which are counter to those of the operator and which seek to return the guide tool 12 to the position setpoint and the orientation setpoint once no force is exerted by the operator. The level of flexibility can be adjustable, for example, by a stiffness parameter or distance parameter.

Figure 3:
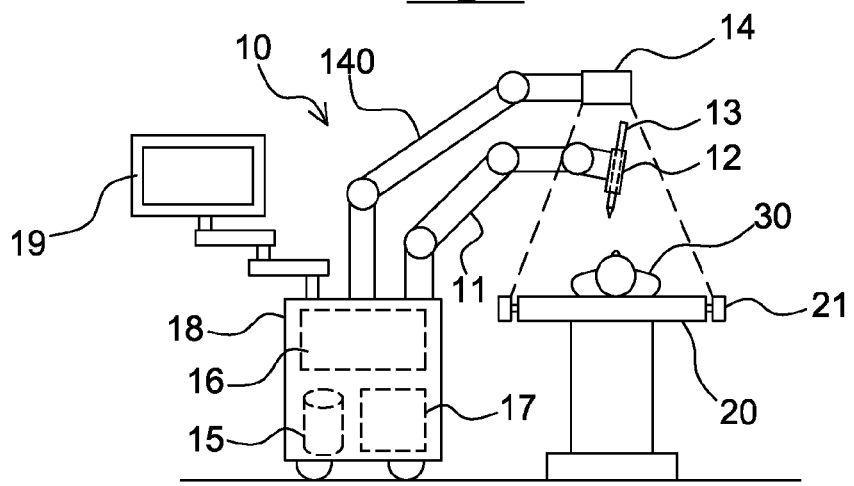
FIG. 3 shows a schematic view of another embodiment of a robotic device.

FIG. 3 shows schematically a preferred embodiment in which the robotic device 10 has a man-machine interface device 19. In the example illustrated in FIG. 3, the man-machine interface device 19 is a display screen, preferably a touch screen. The man-machine interface device 19 allows the operator to control the robotic device 10 and, if appropriate, to view images relating to the medical procedure that is to be performed. For example, the man-machine interface device 19 can be used when planning the medical procedure, in order to establish the trajectory of the medical instrument 13, or to visualize the progress of the medical instrument 13 in the body of the patient 30, for example by displaying the real-time position or almost real-time position of the medical instrument 13 with respect to the position of the target point in the reference frame. The man-machine interface device 19 can also be used to display the images supplied by the image capture system 14.

In the example illustrated in FIG. 3, the man-machine interface device 19 is carried by a mobile carriage 18 which likewise carries the robot arm 11. According to other examples, there is nothing to exclude having the man-machine interface device 19 carried by a separate console, or having it mounted on a rail of the operating table 20, for example removably. Moreover, other man-machine interface devices 19 can be considered alternatively or in addition. For example, the man-machine interface device 19 can comprise a mouse, a keyboard, a touchpad, a joystick, a contactless movement detection module which registers the movements of the hand, fingers, head or eyes of the operator, or a voice-activated control module, etc. In addition, 2D and/or 3D goggles can also replace or supplement the display screen.

In order to ensure the safe use of the robotic device 10, the man-machine interface device 19 can also comprise an acknowledgement module (wired or wireless pedal, box-knob, remote control, switch on the robot arm 11) in order to safeguard the movements of the robot arm 11, which are then subject to the activation of said acknowledgement module.

In preferred embodiments, the processing circuit 17 is configured to determine, or to help the operator determine, the trajectory of the medical instrument 13 on the basis of the images of the patient. In the description below, a non-limiting example of implementation of the robotic device 10 is described for planning a medical intervention that requires introducing the medical instrument into the body of the patient 30.

The medical intervention can be defined, for example, by the trajectory, the medical instrument 13 to be used, and the treatment parameters. The trajectory is composed, for example, of a target point situated in the organ to be treated, and of a point of entry situated at the skin, for example. The medical instrument 13 is defined by several properties such as its length, its diameter, its 3D geometric shape, etc. The treatment parameters can include settings of an ablation technology, for example the power of the delivered current, the treatment time, the diameter of the zone, the distance margins, etc.

The robotic device 10 can, for example, download images of the patient 30 (CT scan, PET (positron emission tomography) scan, MRI scan, X-ray, ultrasound, etc.) from the hospital system or from an external system (cloud computing) or from an external storage medium (USB, CD, DVD, etc.) and allow the images to be viewed, for example on the man-machine interface device 19, in two-dimensional sectional planes, and images reconstructed in three dimensions. For example, algorithms of rigid and non-rigid registration allow several images of the same patient 30 to be merged in order to provide the operator with all of the anatomical and functional information that is needed for planning the medical intervention. The operator can then plan one or more trajectories, depending on the medical intervention that is to be performed. In the case of an ablation by irreversible electroporation, for example, the robotic device 10 makes it possible to create trajectories that are exactly parallel, in order to optimize the efficacy of the treatment.

The positions of the target point and of the point of entry of the trajectory are, for example, identified manually in the images by the operator. The trajectory of the medical instrument 13 in the anatomy can be visualized in the images and modified in order to ensure that the end of the medical instrument 13 reaches an optimal target point and that the insertion of the medical instrument 13 does not damage sensitive anatomical structures between the point of entry and the target point. To facilitate the decision process during planning, the robotic device 10 can integrate segmentation algorithms which automatically identify the contours and volumes of certain organs of interest, nerves, arteries, veins and vessels, bones, and lesions to be treated. Alternatively, the robotic device 10 can automatically determine the target point and the point of entry. For example, the target point is calculated by shape recognition methods and on the basis of parameters of the treatment and of the volume of the target lesion. The point of entry can be calculated by methods for optimization of criteria such as the distance between the trajectory of the medical instrument 13 and sensitive anatomical structures and the position with respect to preferred zones of insertion defined at the skin. Alternatively or in addition, the robotic device 10 can, during its use, also accumulate large quantities of planning data which it reuses and analyzes in order to propose, via an artificial intelligence algorithm, a selection of optimal points of entry and target points.

In preferred embodiments, the processing circuit 17 is configured to regulate, or to help the operator regulate, parameters of the treatment to be performed during the medical intervention, by simulating the effects of said parameters on the basis of images of the patient. For example, from the treatment parameters, the trajectory information and the medical instruments 13, it is possible for the robotic device 10 to calculate the effects of the treatment on the anatomy and to permit visualization of a precise simulation on the images of the patient 30. For thermal ablation for example, the calculation can in particular take into account the presence of adjacent vessels and their cooling impact (heat-sink effect). The operator can then adjust the planning data in order to optimize the clinical result of the treatment.

The planning process described above thus makes it possible to plan a wide variety of medical procedures such as laser surgery, ablation by cryotherapy, radiofrequency, microwaves or electroporation, curie therapy, endoscopy, and any technique requiring the insertion of one or more medical instruments 13 into the body of a patient 30. The planning process described above also makes it possible to plan a wide variety of medical procedures that do not require insertion of a medical instrument 13 into the body of a patient 30, for example in the case of a treatment by focused ultrasound.

All of the data needed for planning can be safeguarded by the robotic device 10 in storage means of the processing circuit 17 or in the storage medium 15, or on an external storage medium and recharged subsequently either in order to modify elements or to execute the treatment on the day of the operation with the robotic device 10.

An example is now described of the use of the robotic device 10 for performing a medical procedure which has been planned beforehand and which requires insertion of a medical instrument 13 into the body of the patient 30.

In order to commence the operation, the robotic device 10 is brought into the theater and placed alongside the patient 30. In the case of a robot arm 11 mounted on a mobile carriage 18, the robotic device 10 is immobilized prior to a phase of registering the position of the patient 30.

The operator then controls the robotic device 10, for example by way of the man-machine interface device 19, in order to initiate the phase of registering the patient 30. The phase of registering the patient 30 aims to determine the position of the patient 30 in the reference frame associated with the robotic device 10, but also the position of the point of entry and the target point, and also the position setpoint and the orientation setpoint of the guide tool 12, by using the biomechanical model, the position information supplied by the image capture system 14, and the planned trajectory.

Once the position of the patient 30 is known and is coordinated with the pre-operative images, the operator initiates the positioning phase, which aims to place the guide tool 12 in the position setpoint and the orientation setpoint suitable for the medical intervention that is to be performed.

For example, the robotic device 10 takes account of the dimensions of the guide tool 12, the position of the point of entry and the direction to the target point in order to automatically position the robot arm 11 in such a way that the guide tool is aligned on the chosen trajectory, at a safe distance from the adjustable point of entry. The operator can then control the robot arm 11, for example in the collaborative mode, in order to adjust the position of the guide tool 12 as close as possible to the point of entry while maintaining the alignment on the trajectory, then in order to block the movements of the robot arm 11 and then insert a medical instrument 13 through the guide tool 12.

In preferred embodiments, the robotic device 10 has a registering device (not shown in the figures). Thus, by virtue of the robotic device 10, the operator can precisely register the point of entry on the skin of the patient at which an incision is to be made. For example, the device for registering the point of entry corresponds to a medical instrument with an atraumatic tip, which is inserted into the guide tool 12, or to a laser targeting module integrated in a medical instrument 13 or in the guide tool 12.

After the incision has been made, the operator can initiate the guiding phase by inserting the medical instrument 13 through the guide tool 12 until the end of the medical instrument reaches the planned target point. The control of the depth of insertion can be based simply on the length of the medical instrument 13 and/or on a mechanical stop system integrated in the guide tool 12. Alternatively or in addition, the guide tool 12 can have a sensor for indicating the depth of insertion of the medical instrument 13. The robotic device 10 can then display, in real time or almost in real time, the position of the medical instrument 13 in the images and can supply messages to the operator when the target point is near, is reached or has been passed. In another variant, the medical instrument 13 is attached mechanically to the guide tool 12, and the robot arm 11 automatically inserts the medical instrument 13 as far as the planned target point.

During the insertion, the processing circuit 17 can use the biomechanical model of the patient 30 to estimate the local deformations of the organs or anatomical structures through which the medical instrument 13 passes and to take these deformations into account for updating the position of the target point.

Depending on the requirements of the operation during the guiding phase, the robotic device 10 is activated, for example, in a tracking mode or a collaborative tracking mode in order to maintain the position of the guide tool 12 with respect to the targeted anatomy, irrespective of the movements of the patient 30. The robotic device 10 can also be activated in a collaborative mode during the guiding phase, by application or non-application of geometric constraints. The collaborative mode, constrained on the axis of the trajectory, is useful for example in the performance of staged biopsies.

When the medical instrument 13 has reached the target point, the planned medical intervention can be carried out for diagnostic purposes or for localized treatment: for example the sampling of tissue for a biopsy, the delivery of liquid nitrogen for a cryotherapy, the generation of an electric current for a radiofrequency ablation, the injection of radioactive sources for a curie therapy, the direct viewing of the anatomy and the insertion of medical instruments into the work channel of the endoscope for endoscopic surgery, etc.

At any moment during or after the guiding phase, the operator can verify the correct execution of the insertion of the medical instrument 13 via control images. Depending on the equipment available to the hospital and in the operating theater, the anatomical zone of interest can be examined using a fixed or mobile imaging apparatus (CT scanner, MRI scanner, radiology C-arc, ultrasound probe, etc.). In preferred embodiments, the images are transferred directly to the robotic device 10, of which the processing circuit 17 comprises, for example, registration algorithms for automatically merging these intra-operative images with the pre-operative images. The robotic device 10 then displays the planning information superposed on the intra-operative images in order to evaluate the progress or the efficacy of the treatment and to determine the corrections that have to be made if necessary.

In preferred embodiments of the invention, the processing circuit 17 can also comprise segmentation algorithms for automatically identifying a necrosis zone, comparing it with the planned zone, calculating and displaying the margins obtained in terms of diameter or volume, and indicating the diameter or volume still to be treated. Optionally, the robotic device 10 can also provide the information needed for complementary treatment, such as the positions and parameters of one or more additional ablation trajectories.

More generally, it will be noted that the embodiments and uses considered above have been described as non-limiting examples and that other variants are therefore conceivable.

In particular, the invention has been described on the basis of the medical instrument 13 being mounted on the robot arm 11 by way of a guide tool 12. It will be noted, however, that the robotic device 10 can also be used without employing a guide tool 12. For example, the use of a guide tool 12 is not necessary in the case where the medical instrument 13 does not have to be introduced into the body of the patient 30, for example in the case of external treatment by focused ultrasound. In addition, in the case where the medical instrument 13 has to be inserted into the body of the patient 30, the use of a guide tool 12 is required especially if it is the operator who inserts the medical instrument 13 into the body of the patient 30, but it is not necessarily required if it is the robot arm 11 that automatically inserts the medical instrument 13 into the body of the patient 30.

The invention claimed is:

1. A robotic device for performing a medical intervention on an anatomical area located inside a body of a patient using a medical instrument, comprising:
    a robot arm having several degrees of freedom and having an end configured to receive the medical instrument,
    an image capture system configured to capture position information concerning anatomy of the body of the patient,
    a storage medium comprising a biomechanical model of anatomical structures of a human body,
    a processing circuit configured to determine a position setpoint and an orientation setpoint for the medical instrument based on the biomechanical model, the position information concerning the anatomy of the body of the patient and a trajectory to be followed by the medical instrument in order to perform the medical intervention, and wherein the processing circuit is further configured to determine a position of a point of entry and a position of a target point of the trajectory in a reference frame, and
    a control circuit configured to control the robot arm to place, or help to place, the medical instrument in the position setpoint and the orientation setpoint,
    wherein the image capture system includes at least one non-contact device configured to capture position information without contact with the body of the patient,
    wherein the captured position information is based on a position of the anatomy of the patient, and a calculation for coordinating the biomechanical model with information concerning the position of the anatomy of the patient are carried out in real time;
    wherein the determined position of the point of entry and the position of the target point of the trajectory in a reference frame is based on deformations of anatomical structures of the patient with respect to the anatomical structures of the patient under consideration to determine the trajectory; and
    wherein the position of the point of entry and the position of the target point in the reference frame are updated in real time to monitor movements and deformations of the anatomical structures of the patient.

2. The robotic device of claim 1, wherein the biomechanical model of the anatomical structures of the human body includes a thoracic zone or an abdominal zone or a pelvic zone.

3. The robotic device as claimed in claim 1, wherein the image capture system is of a non-irradiating type.

4. The robotic device of claim 1, wherein the at least one non-contact device comprises:
    a stereoscopic camera,
    a structured-light camera,
    a time-of-flight camera, or
    a depth measurement camera.

5. The robotic device of claim 1, wherein the image capture system is further configured to supply position information corresponding to a position of an outer surface of the body of the patient.

6. The robotic device of claim 1, wherein the control circuit is further configured to control the robot arm according to at least one of a following mode:
    an automatic mode,
    a collaborative mode,
    an automatic tracking mode, or
    a collaborative tracking mode.

7. The robotic device of claim 1, wherein the processing circuit is further configured to determine or assist in determining the trajectory of the medical instrument based on an image of the body of the patient.

8. The robotic device of claim 1, wherein the processing circuit is further configured to regulate or assist in regulating parameters of a treatment that is to be carried out during the medical intervention, by simulating effects of said parameters based on an image of the body of the patient.

9. The robotic device of claim 1, further comprising a guide tool configured to guide the medical instrument, fixed or intended to be fixed to an end of the robot arm.

10. The robotic device of claim 1, further comprising at least one man-machine interface device comprising:
    a display screen,
    a touch sensitive display screen,
    a keyboard,
    2D or 3D goggles,
    a joystick,
    a movement detection module, or
    a voice-activated control module.

11. The robotic device of claim 1, further comprising at least one device for registering the point of entry comprising:
    a medical instrument with an atraumatic tip, or
    a laser targeting module.

12. The robotic device of claim 1, wherein the medical instrument comprises:
    a biopsy needle,
    a catheter,
    an endoscope,
    a treatment instrument using focused ultrasound,
    a laser treatment instrument,
    an instrument for treatment by cryotherapy,
    an instrument for treatment by radiofrequency,
    an instrument for treatment by electroporation, or
    an instrument for treatment by curie therapy.

13. The robotic device of claim 1, further comprising a mobile carriage carrying the robot arm, the mobile carriage comprising an immobilizing means.

14. A method for treatment or diagnosis of the patient comprising positioning the medical instrument internally or externally to the body of the patient using the robotic device of claim 1, and treating or diagnosing the patient.

15. The robotic device of claim 9, wherein the robot arm is configured to exert forces which are counter to those of an operator and which seek to return the guide tool to the position setpoint and the orientation setpoint once no force is exerted by the operator.

16. The robotic device of claim 1, wherein the processing circuit further includes instructions for coordinating the biomechanical model with the position information concerning the anatomy of the patient and the position information supplied by the image capture system, and
    wherein the processing circuit is further configured to determine a position and orientation of the patient in a reference frame associated with the robotic device.

17. The robotic device of claim 16, wherein algorithms are configured to propagate movements of a surface of a skin of the patient to an internal volume and to calculate a position of internal anatomical structures, and to determine a position and a deformation of an organ from information concerning a position of vessels of the organ or to determine the position and the deformation of the organ from information concerning a position of an outer surface of the organ.

* * * * *